United States Patent [19]

Mattei et al.

[11] 4,443,430

[45] Apr. 17, 1984

[54] SYNTHETIC ABSORBABLE HEMOSTATIC AGENT

[75] Inventors: Frank V. Mattei, Piscataway, N.J.; Namassivaya Doddi, Upland, Calif.

[73] Assignee: Ethicon, Inc., Somerville, N.J.

[21] Appl. No.: 442,218

[22] Filed: Nov. 16, 1982

[51] Int. Cl.³ .................... A61K 31/74; C08G 63/08
[52] U.S. Cl. .................................... 424/78; 528/354; 528/358
[58] Field of Search ................... 424/78; 528/354, 358

[56] References Cited

U.S. PATENT DOCUMENTS

| 2,668,162 | 2/1954 | Lowe | 528/354 |
|---|---|---|---|
| 2,772,999 | 12/1956 | Masci et al. | 167/84 |
| 3,395,217 | 7/1968 | Statt | 424/81 |
| 3,636,956 | 1/1972 | Schneider | 128/335.5 |
| 4,137,921 | 2/1979 | Okuzumi et al. | 128/335.5 |
| 4,186,448 | 2/1980 | Brekke | 128/296 |
| 4,201,216 | 5/1980 | Mattei | 128/335.5 |

FOREIGN PATENT DOCUMENTS 1584080 12/1977 United Kingdom .

*Primary Examiner*—Leonard Schenkman
*Attorney, Agent, or Firm*—Leonard Kean

[57] ABSTRACT

A synthetic absorbable hemostatic agent for use in the control of osseous hemorrhage, comprising a copolymer of lactide and glycolide containing from about 30% to 70% lactide on a molar basis, and having a molecular weight such that it possesses a putty-like consistency at room temperature. The preferred agent has a lactide/glycolide molar ratio of 65:35 and a molecular weight of between 2000 and 2500 Dalton. The agent may also be mixed with a biocompatible base.

16 Claims, No Drawings

SYNTHETIC ABSORBABLE HEMOSTATIC AGENT

BACKGROUND OF THE INVENTION

1. Field of the Invention

This invention relates to a bone sealant and more particularly to a synthetic absorbable lactide/glycolide copolymer used for the control of osseous hemorrhage. (The term "lactide/glycolide copolymer" used herein, is intended to refer to the copolymer derived from lactide/glycolide monomers as starting materials.) This invention also relates to mixtures of the copolymer in a biocompatible base, and also to the process for applying the bone sealant.

2. Description of Prior Art

Various substances and compositions have been employed by members of the medical profession to control bleeding from cut bone surfaces. One class of materials used for the control of this type of hemorrhage is called bone wax. Bone waxes are used for the purpose of controlling hemorrhages from the cut surfaces of bones, such as those of the skull, by forcibly smearing the wax over the cut surface so that the material acts mechanically to occlude and seal the open ends of the bleeding osseous vessels and sinuses.

Bone waxes used in surgery today are generally prepared from refined beeswax which has been admixed with other nonabsorbable and water insoluble hydrocarbons and vegetable oils. Certain disadvantages inhere in these bone wax compositions, as for example, relatively poor adhesion properties, and the hard brittle state of the wax at room temperatures requiring use at elevated temperatures. Futhermore, paraffin based commercial bone wax is not absorbed by the body and thus remains at the site of application for long periods of time. As a result the wax acts as a foreign body, tending to make it difficult for the body to fight infection and inflammatory reactions that may be introduced in the surrounding tissue, and it also interferes with bone regrowth.

In order to overcome the latter problem, British Pat. No. 1,584,080 discloses an absorbable hemostatic bone sealant, which contains the active components collagen and fibrin. However, the composition of British Pat. No. 1,584,080 suffers from the disadvantage that its storage conditions must be controlled in order to retain desirable aesthetic and tactile properties, since biological materials of animal origin are used.

U.S. Pat. No. 3,395,217 discloses nonabsorbable bone wax compositions comprised of low molecular weight ethylene copolymer waxes containing from about 15 to about 40 percent by weight of another unsaturated consituent and having molecular weights in the range of 1000 to 4000. These waxes have a semisolid consistency such that they can be kneaded between the fingers when at room temperature and have the right amount of tack and adhesion so that they can be easily manipulated in the hands of the surgeon or applied by any suitable applicator such as a gloved finger, spatula or appropriate disposable applicator.

U.S. Pat. No. 2,722,999 describes an absorbable bone wax comprised of a water soluble innocuous base and free acid cellulose glycolic acid ether or free acid cellulose hydroxypropionic acid ether as a hemostatic agent. The composition also preferably contains a tackifier such as cellulose glycolic acid ether salt or cellulose hydroxypropionic acid ether salt (preferably sodium salt) and water as a plasticizer. It should be noted that cellulose and its derivatives are generally not biologically degradable, but merely soluble, and, if the molecular weights are high enough, may not even pass through the kidneys.

The Annals of Surgery 132, 1128 (1950) describes an absorbable hemostatic bone wax containing powdered oxidized cellulose as the hemostatic agent in a base of polyethylene glycol. The base is a mixture of high and low molecular weight polyethylene glycols selected to provide the malleability and consistency of material desired for this use. However, polyethylene glycols are completely water soluble. When they comprise the largest percentage of the mixture, the mixture becomes slimy in the area wet with tissue fluids, this being true of any water soluble base. In addition, a large percentage of polyethylene glycols give a pronounced tissue reaction.

U.S. Pat. No. 4,186,448 discloses a one-piece molded body member for filling and covering a bone void or soft tissue deficiency, which body member attracts blood in fluid suspension by capilliary action until clotting forms which ultimately leads to the formation of tissue and/or bone. The body member is made of a biodegradable material such as polylactic acid.

U.S. Pat. No. 4,137,921 discloses a relatively high molecular weight, fiber forming, copolymer of lactide and glycolide. This high molecular weight material would not be at all suitable as a bone wax.

The present invention provides a new synthetic absorbable bone sealant which is a putty-like semisolid at room temperature. The softness of the sealant allows the material to be packaged in a syringe, plastic or coated paper envelope, or aluminum or glass tube from which it may be extruded or dispensed in desired amounts during use. The sealant has sufficient tack so that it adheres to bone surfaces, yet is easily manipulated in the hands of the surgeon without crumbling or sticking to the surgeon's gloves. Considering that known lactide/glycolide copolymers are solid, hard materials it is surprising that the instant copolymer possesses the above-described putty-like properties. Furthermore, the instant copolymer also possesses the advantage of not "setting-up" even after a long period of standing, and it also maintains an aesthetic physical appearance. The instant copolymer may be sterilized by Cobalt 60 (gamma irradiation), avoiding tedious heating to high temperatures.

It is to be noted that polymers derived from lactide/glycolide (such as the instant copolymers) have a good history of in vivo absorption due to hydrolysis of ester bonds, have shown minimum tissue reaction and are nontoxic (lactic and glycolic acids are both body metabolites). See U.S. Pat. No. 3,636,956.

SUMMARY

The bone sealant of the present invention comprises a copolymer of lactide and glycolide containing from about 30 to 70 percent lactide on a molar basis, having a molecular weight such that it is workable and softenable by hand to bring about a putty-like consistency at room temperature. The sealant has a consistency of a semisolid which is extrudable from a large orifice syringe. The sealant is packaged in a syringe, plastic envelope or aluminum tube and is sterilized by radiation. During use, small amounts of the sealant may be extruded from the package as required by the surgeon.

The sealant is effective to control osseous hemorrhage from cut bone and does not interfere with subsequent healing and rejoining of bone parts.

DESCRIPTION OF PREFERRED EMBODIMENTS

The lactide/glycolide copolymer of the present invention possesses an inherent viscosity range between 0.03 and 0.1 and preferably contains between 60% and 70% lactide on a molar basis. The most preferred copolymer is one in which the lactide/glycolide ratio is 65/35 on a molar basis. In the latter instance, the preferred molecular weight lies between 2000 and 2500 Dalton. The inherent viscosity of said 65/35 lactide/glycolide copolymer is preferably about 0.05. This copolymer is workable and softenable by hand to bring about a putty-like consistency at room temperature, permitting a surgeon to spread the agent with his fingers or a spatula over the cut surface of a bone. At the same time, the agent has a tackiness which permits it to adhere readily to the bleeding bone surface and yet being able to be manipulated without crumbling or sticking to the surgeon's gloves.

The instant bone wax is preferably used alone. However, Applicant has found that the instant bone wax may be mixed with a biocompatible base which is a non-chemically reacting material capable of forming a solution or a gel with the agent. Suitable biocompatible bases are calcium stearate, glyceryl monostearate and water. One to five percent by weight of calcium stearate may be added, based on the total weight of the resultant composition. A further suitable composition is one which includes from 5 to 30 percent by weight of glyceryl monostearate, based upon the total weight of the resultant composition.

Applicant has found that the following mixtures of 65/35 lactide/glycolide copolymer with various biocompatible bases provide excellent results: (expressed as percentages by weight)

1. 90% copolymer; 10% glyceryl monostearate
2. 85% copolymer; 15% glyceryl monostearate
3. 95% copolymer; 5% calcium stearate
4. 89% copolymer; 10% glyceryl monostearate and 1% calcium stearate
5. 92.5% copolymer; 5% glyceryl monostearate and 2.5% calcium stearate The following composition also provides excellent results, but requires more working with the fingers than do the other compositions listed above:

47.5% copolymer; 30.0% glyceryl monostearate; 2.5% calcium stearate and 20.0% water.

In general, the present invention includes an absorbable hemostatic composition for use in the control of osseous hemorrhage, comprising by weight:

85 to 95% of a 65/35 molar lactide/glycolide copolymer, from 1 to 5% calcium stearate and the remainder, if any, being glyceryl monostearate.

The present invention also includes within its ambit the copolymer per se of about 65% lactide and about 35% glycolide on a molar basis, having an inherent viscosity of between about 0.03 and 0.1, the preferred copolymer having an inherent viscosity of about 0.05.

Also included within the scope of the present invention is the process for the control of bleeding from cut bone surfaces, which comprises applying to the cut bone surface a copolymer of lactide and glycolide containing from about 30 to 70% lactide on a molar basis, having a molecular weight such that it is workable and softenable by hand to bring about a putty-like consistency at room temperature, the agent having a tackiness sufficient for it to adhere readily to a bloody bone surface and yet being able to be manipulated without crumbling or sticking to the surgeon's gloves.

The present process is preferably carried out utilizing a copolymer containing about 65% lactide and 35% glycolide on a molar basis, the molcular weight of the copolymer being between about 2000 and 2500 Dalton.

POLYMERIZATION PROCEDURE

The copolymer of the present invention is prepared by a random copolymerization of optically active lactide and glycolide monomers, with the lactide component comprising between 30 and 70% of the monomer mixture. The polymerization is carried out in a conventional manner using a polymerization reactor equipped with heating and stirring means and in the presence of a polymerization catalyst such as stannous octoate. A suitable chain terminator, such as lauryl alcohol, is used in order to limit the molecular weight to a very low level. (It should be noted that the desired consistency of the final product can be varied by varying the lauryl alcohol content or the stannous octoate content or both). The polymerization is conducted with pure and dry reactants and under an atmosphere of dry nitrogen at a temperature sufficient to maintain the reaction mixture in a molten state until the polymerization is complete.

Specific details concerning the polymerization are set forth in the following examples.

Apart from synthesizing the copolymer from the respective monomers, the desired low molecular weight copolymer of 65:35 lactide/glycolide may be obtained by hydrolyzing a known high molecular weight copolymer in moist air at about 50° C. until it becomes plastic and sticky, followed by thorough drying.

The following examples are provided to further illustrate preferred embodiments of the present invention. All inherent viscosity measurements are carried out in hexafluoroisopropanol at a concentration of 0.1 g/dl and at a temperature of 25° C.

EXAMPLE 1

Lactide/Glycolide Copolymer

The reaction vessel is charged with purified L(—)lactide and purified glycolide monomers in the molar ratios of 65 to 35. Stannous octoate is added as the catalyst so as to give a monomer to catalyst ratio of 15,000/1, while glycolic acid is added as the chain terminator in a monomer to glycolic acid ratio of 108/1. After completing the charge, the reactor is pumped down to 100–200$\mu$, then released with nitrogen and polymerization is conducted by heating 2½ hours at 185° C. Analysis of the resulting polymer indicates 98% completion of the reaction, and an inherent viscosity of 0.6. It is glassy in appearance, and is very hard in spite of the fact that it is noncrystalline.

This relatively high molecular weight copolymer is then hydrolyzed in moist air at about 50° C. until it becomes plastic and sticky. This is followed by thorough drying. The product has a number average molecular weight of 2300.

EXAMPLE 2

Very Low Molecular Weight Lactide/Glycolide Copolymer 187.2 Gm (1.3 mole) of purified L(−)lactide and 81.2 gm (0.7 mole) of purified glycolide are placed in a 500 ml glass ampoule provided with a magnetic stirring bar. This monomer charge gives a lactide to glycolide molar ratio of 65 to 35. In addition, 53.0 gms of dodecanol (lauryl alcohol) are added as a chain terminator (16.5% by weight of the entire charge). This large amount of dodecanol is an important factor in limiting the molecular weight to a very low level. The last addition is 5.04 ml of stannous octoate solution in toluene as the catalyst (molar ratio of monomer to catalyst=12,000 to 1). The ampoule and contents are pumped down to a vacuum of about 50-100μ with alternate purges of nitrogen, and finally sealed @ 7-10 inches of vacuum/nitrogen. It is polymerized in a 185° C. oil bath for 3 hours, and after cooling it is poured (with the help of slight warming to about 40°-45° C.) in a tray and devolatilized 72 hours @ 60° C. in vacuum.

NMR analysis shows that the dodecanol in the above polymer is completely reached as part of the chain. The polymer has a light tan color, with the consistency of a firm glazier's window putty, and becomes softer and yields to working with the fingers the more it is handled.

A variation of the above sealant is prepared by adding to it 5% by weight of finely powdered calcium stearate and mixing it in thoroughly.

Both of the above preparations are warmed up, poured into collapsible tin squeeze-type tubes and sterilized via Cobalt 60 (gamma irradiation).

EXAMPLE 3

A study was conducted to determine the in vivo tissue reaction, toxicity, and absorption of compositions X and Y, as well as the pattern of bone regrowth in response to their presence. Composition X was a low molecular weight 65/35 lactide/glycolide copolymer plus 5 weight % of calcium stearate, while composition Y was the aforementioned 65/35 lactide/glycolide copolymer alone (prepared according to Example 2).

Eight healthy, mature, female Beagles, weighing 8 to 10 kilograms were anesthetized. After appropriate surgical preparation, a midline incision was made through the skin on the head of each dog. The skin was then retracted so that the temporalis muscle on one side was exposed. This muscle was incised about 5 mm from its original so that it could be reflected, exposing the underlying parietal bone. A number of surgically-induced burr holes were made in the calvarium (full-thickness, exposing but not penetrating the dura, approximately 7.0 mm diameter) and were filled with the test materials. The temporalis muscle was then sutured in place and thereafter the contralateral temporalis muscle was similarly incised and reflected. A number of holes were then made in the underlying temporal bone and also filled with the test materials. The skin was then repaired in a routine manner.

An incision was then made over the iliac crest. After exposure of the iliac crest, a number of holes were drilled into this bone, the test materials were then applied and thereafter the skin was closed in a routine manner. The contralateral iliac crest was then exposed, drilled, samples applied, and repaired in the same manner. Both in the calvarium and in the iliac crest appropriate holes were filled with test materials X and Y, and in each case appropriate control holes were left empty.

The appropriate number of dogs were sacrificed on the 28th, 56th, 91st or 119th day following surgery and subjected to a necropsy examination. Gross necropsy examination was made of all sites. The calvaria and iliac crests were removed in toto. Individual sections of calvarium, each containing a burr hole, then were made with a band saw. Each hole was divided in half and both sections fixed in 10% buffered formalin. One half was decalcified, processed and stained with hematoxylin and eosin. The other half was retained for preparation of undecalcified bone sections if needed. However, only the results, based on the decalcified sections are considered herein.

Clinical Findings

There were no abnormalities of the blood in any of the dogs after surgery. All dogs in the study had large swellings near their incision sites for some time postoperatively. One dog appeared listless forty-one days postoperatively, but had no other observable abnormalities. Forty-three days postoperatively, the dog's condition worsened, involving CNS abnormalities and the dog died the following day. Necropsy revealed a cerebral abscess beneath the hole containing material X.

Histopathologic Findings

Calvarium

The sites containing materials X and Y were slowly filled with fibrovascular connective tissue with no evidence of the test materials except for small, faint white spots in some of the sites. Generally, at period 56 days and longer, control sites and the sites containing the synthetic materials became somewhat difficult to identify.

The inflammatory response at 28 days in the sites containing the test materials was of the foreign body type, but moderate to slight in extent. The foreign body reaction in these sites surrounded circular, empty spaces of variable size. The spaces were presumed to have contained the test materials which were lost during histologic preparation. One vacuolar space in one of the dogs was filled with small, round or ovoid, birefringent particles which are considered to be retained material Y. The areas of the calvarial defects not filled by the foreign body reaction generally contained fibrovascular connective tissue.

At 56, 91 and 119 days, the sites containing materials X and Y had minimal to moderate foreign body reactions at these periods. A foreign body reaction associated with vacuolar spaces was observed in the control sites in several dogs at all periods. Generally the vacuolar spaces and inflammatory reactions were restricted to the outer surfaces of the defects. Also, in general, the number of vacuoles and the inflammatory reaction to them tended to diminish from 28 to 119 days.

No evidence of osteogenesis was noted the fibrovascular connective tissue in any of the defects. Extension of new bone into connective tissue of the defect resulted in an apparent reduction in the size of the defect. Compared to the control sites, there was less new bone present in the X and Y defects.

Iliac Crest

Grossly, the periosteal surfaces of the iliac crests were covered by fibrovascular connective tissue. Bone remodeling, i.e., repair of a bone defect by new bone formation, would be expected to proceed more rapidly in cancellous bone, such as that in the iliac crest, than in the denser bone of the calvarium. This contributed to the difficulty in locating the holes in the iliac crest.

COMMENT

The inflammatory response to both of the experimental materials was foreign body in type. Material X appeared to induce a slightly more severe foreign body reaction than material Y. The controls incited the least cellular response of all.

The areas of defects not filled by inflammatory cells were usually filled with fibrovascular connective tissue. New bone formation then occurred only at the calvarial surface, i.e., at the osteotomy surface as well as on both the inner and outer surfaces of the calvarium. Under the conditions of this study, significant differences in the amount of bone formation among the test materials and the controls were not observed. Bony filling of defects was only impeded to a moderate extent by materials X and Y. The overall quality of the reparative process, in order of decreasing acceptability, based on the amount of connective tissue proliferation, reduction in size of the defects and degree of inflammation were: controls; material X and material Y.

SUMMARY

The inflammatory reaction of materials X and Y persisted throughout the 119 day period, but gradually diminished with time. This coincided with the amount of test material remaining in the sites at the various periods, i.e., materials X and Y, while diminishing in amount at each successive period, were still present at 119 days, although a substantial part was gone. It is surmised that absorption would probably have been completed after 150 days.

We claim:

1. A synthetic absorbable hemostatic agent for use in the control of osseous hemorrhage, comprising a copolymer of lactide and glycolide containing from about 30% to 70% lactide on a molar basis, having a molecular weight such that it is workable and softenable by hand to bring about a putty-like consistency at room temperature, the agent having a tackiness sufficient for it to adhere readily to a bloody bone surface and yet being able to be manipulated without crumbling or sticking to the surgeon's gloves, said copolymer having an inherent viscosity in hexafluoroisopropanol at a concentration of 0.1 g/dl and at a temperature of 25° C. of between about 0.03 and 0.1.

2. A synthetic absorbable hemostatic agent for use in the control of osseous hemorrhage, comprising a copolymer of lactide and glycolide containing from about 60% to 70% lactide on a molar basis and having a molecular weight such that it is workable and softenable by hand to bring about a putty-like consistency at room temperature, the agent having a tackiness sufficient for it to adhere readily to a bloody bone surface and yet being able to be manipulated without crumbling or sticking to the surgeon's gloves, said copolymer having an inherent viscosity in hexafluoroisopropanol at a concentration of 0.1 g/dl and at a temperature of 25° C. of between about 0.03 and 0.1.

3. The agent of claim 2 in which the lactide/glycolide ratio is about 65/35 on a molar basis.

4. The agent of claim 2 which includes a biocompatible base which is a non-chemically reacting material capable of forming a solution or gel with said agent.

5. The agent of claim 4 in which the biocompatible base is selected from one or more of the group comprising: calcium stearate, glyceryl monostearate and water.

6. The agent of claim 5, which includes from 1% to 5% by weight of calcium stearate, based on the total weight of the composition.

7. The agent of claim 5, which includes from 5% to 30% by weight of glyceryl monostearate based upon the total weight of the composition.

8. The agent of claim 5 which includes from 1% to 25% by weight of water based on the total weight of the composition.

9. The agent of claim 2 comprising about 65% lactide, the molecular weight of said agent being between about 2000 and 2500.

10. The agent of claim 9 in which the inherent viscosity inhexafluoroisopropanol at a concentration of 0.1 g/dl and at a temperature of 25° C. is about 0.05.

11. A copolymer, comprising about 65% lactide and 35% glycolide on a molar basis, having an inherent viscosity in hexafluoroisopropanol at a concentration of 0.1 g/dl and at a temperature of 25° C. of between about 0.03 and 0.1.

12. The copolymer of claim 11 in which the inherent viscosity in hexafluoroisopropanol at a concentration of 0.1 g/dl and at a temperature of 25° C. is about 0.05.

13. An absorbable hemostatic composition for use in the control of osseous hemorrhage comprising by weight:

85 to 95% of a 65/35 molar lactide/glycolide copolymer in which the inherent viscosity in hexafluoroisopropanol at a concentration of 0.1 g/dl and at a temperature of 25° C. ranges between 0.03 and 0.1, from 1 to 5% calcium stearate and the remainder, if any, being glyceryl monostearate, said composition having a molecular weight such that it is workable and softenable by hand to bring about a putty-like consistency at room temperature, and having a tackiness sufficient for it to adhere readily to a bloody bone surface and yet being able to be manipulated without crumbling or sticking to the surgeon's gloves.

14. A process for the control of bleeding from cut bone surfaces, which comprises applying to the cut bone surface, a copolymer of lactide and glycolide containing from 30% to 70% lactide on a molar basis, having a molecular weight such that it is workable and softenable by hand to bring about a putty-like consistency at room temperature, the agent having a tackiness sufficient for it to adhere readily to a bloody bone surface and yet being able to be manipulated without crumbling or sticking to the surgeon's gloves, said copolymer having an inherent viscosity in hexafluoroisopropanol at a concentration of 0.1 g/dl and at a temperature of 25° C. of between about 0.03 and 0.1.

15. A process for the control of bleeding from cut bone surfaces, which comprises applying to the cut bone surface, a copolymer of lactide and glycolide containing from 60% to 70% lactide on a molar basis and having a molecular weight such that it is workable and softenable by hand to bring about a putty-like consistency at room temperature, the copolymer having a tackiness sufficient for it to adhere readily to a bloody bone surface and yet being able to be manipulated without crumbling or sticking to the surgeon's gloves, said copolymer having an inherent viscosity in hexafluoroisopropanol at a concentration of 0.1 g/dl and at a temperature of 25° C. of between about 0.3 and 0.1.

16. The process of claim 15 in which the copolymer comprises about 65% lactide, the molecular weight of the copolymer being between about 2000 and 2500.

* * * * *